US006942972B2

(12) United States Patent
Farooqui et al.

(10) Patent No.: US 6,942,972 B2
(45) Date of Patent: Sep. 13, 2005

(54) EFFICIENT SYNTHESIS OF PROTEIN-OLIGONUCLEOTIDE CONJUGATES

(75) Inventors: Firdous Farooqui, Brea, CA (US); Parameswara Meda Reddy, Brea, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 418 days.

(21) Appl. No.: 10/032,592

(22) Filed: Oct. 24, 2001

(65) Prior Publication Data

US 2003/0092901 A1 May 15, 2003

(51) Int. Cl.[7] .................... C12Q 1/68; C12N 9/96; C12N 11/02
(52) U.S. Cl. .................... 435/6; 435/7.9; 435/177; 435/188; 530/391.1; 530/391.9; 530/409
(58) Field of Search .................... 435/7.9, 6, 177, 435/188; 530/391.1, 391.9, 409

(56) References Cited

U.S. PATENT DOCUMENTS

| | | | |
|---|---|---|---|
| 4,526,871 A | 7/1985 | Avrameas et al. | 436/504 |
| 4,683,194 A | 7/1987 | Saiki et al. | 436/6 |
| 4,683,202 A | 7/1987 | Mullis | 435/91 |
| 4,946,778 A | 8/1990 | Ladner et al. | 435/69.6 |
| 5,270,184 A | 12/1993 | Walker et al. | 435/91.2 |
| 5,316,906 A | 5/1994 | Haugland et al. | 435/4 |
| 5,427,930 A | 6/1995 | Birkenmeyer et al. | 435/91.52 |
| 5,441,867 A * | 8/1995 | Garman et al. | 435/6 |
| 5,443,986 A | 8/1995 | Haughland et al. | 435/4 |
| 5,455,166 A | 10/1995 | Walker | 435/91.2 |
| 5,552,541 A | 9/1996 | Adams | 536/22.1 |
| 5,605,800 A | 2/1997 | Kourilsky et al. | 435/6 |
| 5,648,213 A | 7/1997 | Reddy et al. | 435/6 |
| 5,698,411 A | 12/1997 | Lucas et al. | 435/29 |
| 5,733,733 A | 3/1998 | Auerbach | 435/6 |
| 5,854,033 A | 12/1998 | Lizardi | 435/91.2 |
| 5,876,928 A | 3/1999 | Kourilsky et al. | 435/6 |
| 5,955,262 A | 9/1999 | Kourilsky et al. | 435/6 |
| 5,976,822 A | 11/1999 | Landrum et al. | 435/23 |
| 5,989,823 A | 11/1999 | Jayasena et al. | 435/6 |
| 6,090,552 A | 7/2000 | Nazarenko et al. | 435/6 |
| 6,124,120 A | 9/2000 | Lizardi | 435/91.2 |
| 6,143,495 A | 11/2000 | Lizardi et al. | 435/6 |
| 6,180,338 B1 | 1/2001 | Adams | 435/6 |
| 6,197,513 B1 | 3/2001 | Coull et al. | 435/6 |
| 6,207,368 B1 | 3/2001 | Adams | 435/6 |
| 6,218,152 B1 | 4/2001 | Auerbach | 435/91.2 |
| 6,251,621 B1 | 6/2001 | Lawrence et al. | 435/18 |
| 6,261,808 B1 | 7/2001 | Auerbach | 435/91.1 |
| 2003/0045694 A1 * | 3/2003 | Chait et al. | 536/23.1 |

FOREIGN PATENT DOCUMENTS

| | | | | |
|---|---|---|---|---|
| EP | A 320308 | 11/1993 | | C12Q/1/68 |
| EP | A 439182 | 4/1996 | | C12Q/1/68 |
| EP | 641351 | 10/1996 | | C07H/15/26 |

OTHER PUBLICATIONS

Bhattacharyya S.P., et al., "Structural analysis of DNA cleaved in vivo by bacteriophage T4 terminase," *Gene* Aug. 19, 1994;146(1):67–72.

Brandtzaeg, 1973, "Conjugates of immunoglobulin G with different fluorochromes. I. Characterization by anionic–exchange chromatography," *Scand. J. Immunol.* 1973;2(3):273–90.

Chung E.L., "Chemoprevention of lung cancer by isothiocyanates and their conjugates in A/J mouse," *Exp. Lung Res.* Apr.–May 2001;27(3):319–30.

Ezaki, T. et al., "Simple genetic method to identify viridans group streptococci by colorimetric dot hybridization and fluorometric hybridization in microdilution wells," *J. Clin. Microbiol.* Sep. 1988;26(9):1708–13.

Ghosh SS, et al., "Use of maleimide–thiol coupling chemistry for efficient syntheses of oligonucleotide–enzyme conjugate hybridization probes," *Bioconjug. Chem.* Jan.–Feb. 1990;1(1):71–6.

Gupta R.K., et al., "Adjuvants for human vaccines—current status, problems and future prospects," *Vaccine* Oct 1995;13(14):1263–76.

Hendrickson, R. E.et al., Nucl., Acids Res. 23:522–529 (1994).

Kohler, G. & Milstein, C., "Continuous cultures of fused cells secreting antibody of predefined specificity," *Nature.* Aug. 7, 1975;256(5517):495–7.

Kusunoki, S. et al., "Application of colorimetric microdilution plate hybridization for rapid genetic identification of 22 *Mycobacterium* species," *J. Clin. Microbiol.* Aug. 1991;29(8):1596–603.

Loken and Herzenberg, 1975, "Analysis of cell populations with a fluorescence–activated cell sorter," *Ann. N.Y. Acad. Sci.* Jun. 30, 1975;254:163–71.

Martin R., et al., "A highly sensitive, nonradioactive DNA labeling and detection system," 13: *Biotechniques* Dec. 1990;9(6):762–8).

Morrison, S. et al., "Chimeric human antibody molecules: mouse antigen–binding domains with human constant region domains," *Proc. Natl. Acad. Sci. U S A* Nov. 1984;81(21):6851–5.

Oi, V. T. & Morrison, S. L., BioTechniques 4:214–221 (1986).

Riechmann, L. et al., "Reshaping human antibodies for therapy," *Nature* Mar. 24, 1988;332(6162):323–7.

(Continued)

Primary Examiner—Mary E. Ceperley
(74) Attorney, Agent, or Firm—Jeffrey I. Auerbach; Liniak, Berenato & White, LLC

(57) ABSTRACT

The present invention relates to an improved method for forming a protein-oligonucleotide conjugate. The method is particularly amenable for forming antibody-oligonucleotide conjugates. The invention further concerns the conjugate molecules produced using such improved methods.

74 Claims, 2 Drawing Sheets

OTHER PUBLICATIONS

Samoszuk, M.K., et al., "A peroxide–generating immunoconjugate directed to eosinophil peroxidase is cytotoxic to Hodgkin's disease cells in vitro," *Antibody, Immunoconjugates Radiopharmaceuticals* 2(1), 37–45 (1989).

Tramontano, A. et al., "Chemical reactivity at an antibody binding site elicited by mechanistic design of a synthetic antigen," *Proc. Natl. Acad. U S A.* Sep. 1986;83(18):6736–40.

Tyagi, et al., "Molecular beacons: probes that fluoresce upon hybridization," *Nature Biotechnol.* 14(3):303–8 (1996).

Wood, C. R. et al., *Nature* 314:446–449(1985).

Rajur et al, "Covalent protein–oligonucleotide conjugates for efficient delivery of antisense molecules," *Bioconjug Chem.* Nov.–Dec. 1997;8(6):935–940 (1997).

Zhang T.H., et al., "Detection for anti–hantavirus IgM in patient serum with silver enhanced dot immunogold filtration assay," *Zhonghua Shi Yan He Lin Chuang Bing Du Xue Za Zhi* Sep. 2000;14(3):266–7.

* cited by examiner

Oligonucleotide-antibody conjugate

IL-8 Assay on A² Plate

EFFICIENT SYNTHESIS OF PROTEIN-OLIGONUCLEOTIDE CONJUGATES

FIELD OF THE INVENTION

The present invention is in the field of chemistry and biotechnology. The present invention relates to an improved method for forming a protein-oligonucleotide conjugate. The method is particularly amenable for forming antibody-oligonucleotide conjugates. The invention further concerns the conjugate molecules produced using such improved methods.

BACKGROUND OF THE INVENTION

Assays directed to the detection and quantification of physiologically significant materials in biological fluid and tissue samples are important tools in scientific research and in the health care field.

Several different types of assay have been developed that are capable of detecting relatively high concentrations of components of common biological samples such as human serum (Zhang T. H., et al., "Detection for anti-hantavirus IgM in patient serum with silver enhanced dot immunogold filtration assay," Zhonghua Shi Yan He Lin Chuang Bing Du Xue Za Zhi 2000 September; 14(3):266–7). Such assays include high-resolution agarose gel electrophoresis and test procedures based on the catalytic activity of endogenous enzymes (Bhattacharyya S. P., et al., "Structural analysis of DNA cleaved in vivo by bacteriophage T4 terminase," Gene 1994 Aug. 19; 146(1):67–72; Gaillot O.,et al, "Molecular characterization and expression analysis of the superoxide dismutase gene from *Streptococcus agalactiae*," Gene 1997 Dec. 19; 204(1–2):213–8; Trigueros S., et al., "Novel display of knotted DNA molecules by two-dimensional gel electrophoresis," Nucleic Acids Res 2001 Jul. 1; 29(13): E67-7). These methods generally do not have the sensitivity required to detect and quantify the numerous other physiologically important sample constituents which may be present at very low concentrations (e.g., endogenous molecules intimately involved in cellular regulation (hormones, steroids, biochemical messengers); basic structural components of the organism (amino acids, proteins, polysaccharides); genetic material (DNA, RNA); vitamins, drugs and drug metabolites; toxins, pathogens and substances generated by the immune system).

Bioconjugates, such as protein-oligonucleotide conjugates, are employed in a wide variety of molecular biology applications (see, Reddy, U.S. Pat. No. 5,648,213). They are used in diagnostic assays to improve assay sensitivity (U.S. Pat. No. 6,197,513 (Coull, et al.). Such conjugates have traditionally been prepared by methods, such as glutaraldehyde crosslinking, maleimide-thiol coupling (Ghosh S S, et al., "Use of maleimide-thiol coupling chemistry for efficient syntheses of oligonucleotide-enzyme conjugate hybridization probes," Bioconjug Chem 1990 January–February; 1(1):71–6), isothiocyanate-amine coupling (Brandtzaeg, 1973, Scand. J. Immunol. 2: 273–290; Loken and Herzenberg, 1975, Annals N.Y. Acad. Sci. 254: 163–171; U.S. Pat. No. 5,648,213 (Reddy, M. P.); Keller, G. H., et al., "DNA Probes," MacMillan Publishers Ltd., 1989), and Schiff base formation/reduction.

Bioconjugates have served a variety of purposes in modem research. For example, bioconjugates such as oligonucleotides conjugated to antibodies or enzymes have been used as hybridization probes in immunoassays (U.S. Pat. No. 5,648,213 (Reddy, M. P.); Ghosh S S, et al., "Use of maleimide-thiol coupling chemistry for efficient syntheses of oligonucleotide-enzyme conjugate hybridization probes," Bioconjug Chem 1990 January–February; 1(1): 71–6; Keller and Manak, DNA Probes, 2nd Edition (Stockton Press, New York, 1993; Milligan et al, J. Med. Chem., 36: 1923–1937 (1993); Drmanac et al, Science, 260: 1649–1652 (1993); Bains, J. DNA Sequencing and Mapping, 4: 143–150 (1993)). Oligonucleotide-antibody conjugates have also been used as probes in the development of sensitive nucleic acid-based diagnostic assays (Martin R., et al., "A highly sensitive, nonradioactive DNA labeling and detection system," 13: Biotechniques 1990 December; 9(6): 762–8) (Podbielski A, et al., "Identification of group A type 1 streptococcal M protein gene by a non-radioactive oligonucleotide detection method," 14: Med Microbiol Immunol (Berl) 1990; 179(5):255–62; Carpenter W. R., et al., "A transcriptionally amplified DNA probe assay with ligatable probes and immunochemical detection," 9: Clin Chem 1993 September; 39(9):1934–8). Other bioconjugates, such as isothiocyanates (ITCs) conjugates, are used in bioassays as versatile chemopreventive agents (Chung E. L., "Chemoprevention of lung cancer by isothiocyanates and their conjugates in A/J mouse," Exp Lung Res 2001 April–May; 27(3):319–30). Protein-polysaccharide conjugates with reciprocally enhanced immunogenicity have been used in the development of combination vaccines (Gupta R. K., et al, "Adjuvants for human vaccines—current status, problems and future prospects," Vaccine 1995 October; 13(14): 1263–76).

Despite the promise that bioconjugates hold for improving assay sensitivity and simplifying nucleic acid detection schemes, they have not become common place tools in molecular biology and diagnostic applications. The preparation of bioconjugates involves multiple steps that require the protein, oligonucleotide, or both, to be modified with the appropriate linking moiety and then purified before being combined and reacted with each other. Often the modification reaction results in an unstable reactive enzyme or oligomer intermediate that must be purified and used immediately. For these and other reasons the yield of conjugate is highly variable when these techniques are used. Furthermore, reaction times are lengthy, and several purification steps are generally needed to obtain a purified conjugate. Finally, in most instances a portion of the enzymatic activity is lost due to the nature of the chemical reactions, lengthy reaction times, and numerous purification steps.

For these reasons direct conjugates are expensive and difficult to make with reproducible results. This has prevented them from becoming commonplace tools in molecular biology and diagnostic applications despite the promise they hold for improving assay sensitivity and simplifying nucleic acid detection schemes.

Despite such efforts, a need continues for methods that provide a more efficient conjugation of an oligonucleotide to an antibody to improve the sensitivity of oligonucleotide-antibody conjugates as reagents in immunoassays. The present invention is directed to such a need.

SUMMARY OF THE INVENTION

The present invention relates to an improved method for forming a protein-oligonucleotide conjugate. The method is particularly amenable for forming antibody-oligonucleotide conjugates. The invention further concerns the conjugate molecules produced using such improved methods.

In detail, the invention provides a method for producing an oligonucleotide-protein conjugate, wherein the method comprises the steps:

(A) contacting an oligonucleotide having an amino group with a heterofunctional linker, wherein the linker has a first group reactive with the amino group and a second group reactive with a thiol group, the contacting being under conditions sufficient to permit the first group of the heterofunctional linker to become bonded to the amino group of the oligonucleotide, thereby forming an oligonucleotide-heterofunctional linker conjugate; and (B) contacting the oligonucleotide-heterofunctional linker conjugate (A) with a protein having a thiol group reactive with the second group of the heterofunctional linker; the contacting being under conditions sufficient to permit the thiol group of the protein to become bonded to the second group of the heterofunctional linker of the oligonucleotide-heterofunctional linker conjugate, to thereby form the oligonucleotide-protein conjugate.

The invention particularly concerns the embodiment of such methods wherein the amino group is at the 3' end of the oligonucleotide, wherein the amino group is at the 5' end of the oligonucleotide or wherein the amino group is at an internal site of the oligonucleotide.

The invention further concerns the embodiments of such methods wherein step (A) additionally comprises forming the oligonucleotide having the 3', 5' or internal amino group.

The invention further concerns the embodiments of such methods wherein the oligonucleotide having the 3' amino group is formed by synthesizing the oligonucleotide on a 3'-amino CPG solid support.

The invention further concerns the embodiments of such methods, wherein the modified amino group is C7 CPG.

The invention additionally concerns the embodiments of such methods wherein the first group of the heterofunctional linker is an NHS group and wherein the second group of the heterofunctional linker is a maleimide group. The invention additionally concerns the embodiments of such methods wherein the heterofunctional linker is selected from the group consisting of Sulfo-SMCC; Sulfo-EMCS; Sulfo-GMBS; Sulfo-KMUS; Sulfo-MBS; Sulfo-SLAB; Sulfo-SMPB; Sulfo-LC-SMPT; SVSB; SIACX; SIA, SIAXX; and NPIA.

The invention additionally concerns the embodiments of such methods wherein the thiol group of the protein is an iminothiolane moiety and wherein step (B) additional comprises forming the protein having the thiol group.

The invention further concerns an oligonucleotide-protein conjugate produced through the process comprising:

(A) contacting an oligonucleotide having an amino group with a heterofunctional linker, wherein the linker has a first group reactive with the amino group and a second group reactive with a thiol group, the contacting being under conditions sufficient to permit the first group of the heterofunctional linker to become bonded to the amino group of the oligonucleotide, thereby forming an oligonucleotide-heterofunctional linker conjugate; and (B) contacting the oligonucleotide-heterofunctional linker conjugate (A) with a protein having a thiol group reactive with the second group of the heterofunctional linker; the contacting being under conditions sufficient to permit the thiol group of the protein to become bonded to the second group of the heterofunctional linker of the oligonucleotide-heterofunctional linker conjugate, to thereby form the oligonucleotide-protein conjugate.

The invention particularly concerns the embodiment of such oligonucleotide-protein conjugates wherein the amino group is at the 3' end of the oligonucleotide, wherein the amino group is at the 5' end of the oligonucleotide or wherein the amino group is at an internal site of the oligonucleotide.

The invention further concerns the embodiment of such oligonucleotide-protein conjugates wherein the protein is an enzyme (especially alkaline phosphatase, β-galactosidase, horse radish peroxidase, or urease), hapten, immunoglobulin (especially an immunoglobulin that is able to bind to a drug, a receptor, a receptor ligand, or a tumor antigen or an immunoglobulin that is able to an antigen that is characteristic of a pathogen (e.g., a virus, bacteria or fungus), streptavidin, avidin, or a phycobillin protein.

The invention further concerns a method for determining the presence or concentration of a target nucleic acid molecule in a sample which comprises:

(I) contacting the sample with an oligonucleotide-protein conjugate, wherein a sequence of an oligonucleotide portion of the conjugate is selected to be able to hybridize with the target nucleic acid molecule, wherein the oligonucleotide-protein conjugate is produced through the process comprising:

(A) contacting an oligonucleotide having an amino group with a heterofunctional linker, wherein the linker has a first group reactive with the amino group and a second group reactive with a thiol group, the contacting being under conditions sufficient to permit the first group of the heterofunctional linker to become bonded to the amino group of the oligonucleotide, thereby forming an oligonucleotide-heterofunctional linker conjugate; and (B) contacting the oligonucleotide-heterofunctional linker conjugate (A) with a protein having a thiol group reactive with the second group of the heterofunctional linker; the contacting being under conditions sufficient to permit the thiol group of the protein to become bonded to the second group of the heterofunctional linker of the oligonucleotide-heterofunctional linker conjugate, to thereby form the oligonucleotide-protein conjugate;

(II) detecting a protein portion of oligonucleotide-protein conjugate having an oligonucleotide portion hybridized to the target nucleic acid molecule; wherein the detection determines the presence or concentration of the target nucleic acid molecule in the sample.

The invention particularly concerns the embodiment of such method wherein the amino group is at the 3' end of the oligonucleotide, wherein the amino group is at the 5' end of the oligonucleotide or wherein the amino group is at an internal site of the oligonucleotide.

The invention particularly concerns the embodiments of such methods wherein the protein of the oligonucleotide-protein conjugate is an enzyme (especially alkaline phosphatase, β-galactosidase, horse radish peroxidase, or urease), hapten, or immunoglobulin (especially an immunoglobulin that is able to bind to a drug, a receptor, a receptor ligand, or a tumor antigen, or an immunoglobulin that is able to an antigen that is characteristic of a pathogen.

The invention particularly concerns the embodiments of such methods where the target nucleic acid molecule is a nucleic acid molecule of a pathogen or tumor cell.

The invention also concerns a method for determining the presence or concentration of a target analyte in a sample which comprises:

(I) contacting the sample with an oligonucleotide-protein conjugate, wherein a protein portion of the conjugate is selected to be able to bind to the target analyte, wherein the oligonucleotide-protein conjugate is produced through the process comprising:

(A) contacting an oligonucleotide having an amino group with a heterofunctional linker, wherein the linker has a first group reactive with the amino group and a second group reactive with a thiol group, the contacting being under conditions sufficient to permit the first group of the heterofunctional linker to become bonded to the amino group of the oligonucleotide, thereby forming an oligonucleotide-heterofunctional linker conjugate; and (B) contacting the oligonucleotide-heterofunctional linker conjugate (A) with a protein having a thiol group reactive with the second group of the heterofunctional linker; the contacting being under conditions sufficient to permit the thiol group of the protein to become bonded to the second group of the heterofunctional linker of the oligonucleotide-heterofunctional linker conjugate, to thereby form the oligonucleotide-protein conjugate;

(II) detecting an oligonucleotide portion of oligonucleotide-protein conjugate having a protein portion bound to the target analyte; wherein the detection determines the presence or concentration of the target analyte in the sample.

The invention particularly concerns the embodiments of such method wherein the protein of the oligonucleotide-protein conjugate is an enzyme, a receptor, or a receptor ligand.

The invention particularly concerns the embodiment of such method wherein the amino group is at the 3' end of the oligonucleotide, wherein the amino group is at the 5' end of the oligonucleotide or wherein the amino group is at an internal site of the oligonucleotide.

The invention particularly concerns the embodiment of such methods wherein the protein of the oligonucleotide-protein is an enzyme, receptor, receptor ligand, tumor antigen or is characteristic of a pathogen (especially a virus, bacteria or fungus).

DESCRIPTION OF THE PREFERRED EMBODIMENTS

Figure 1:
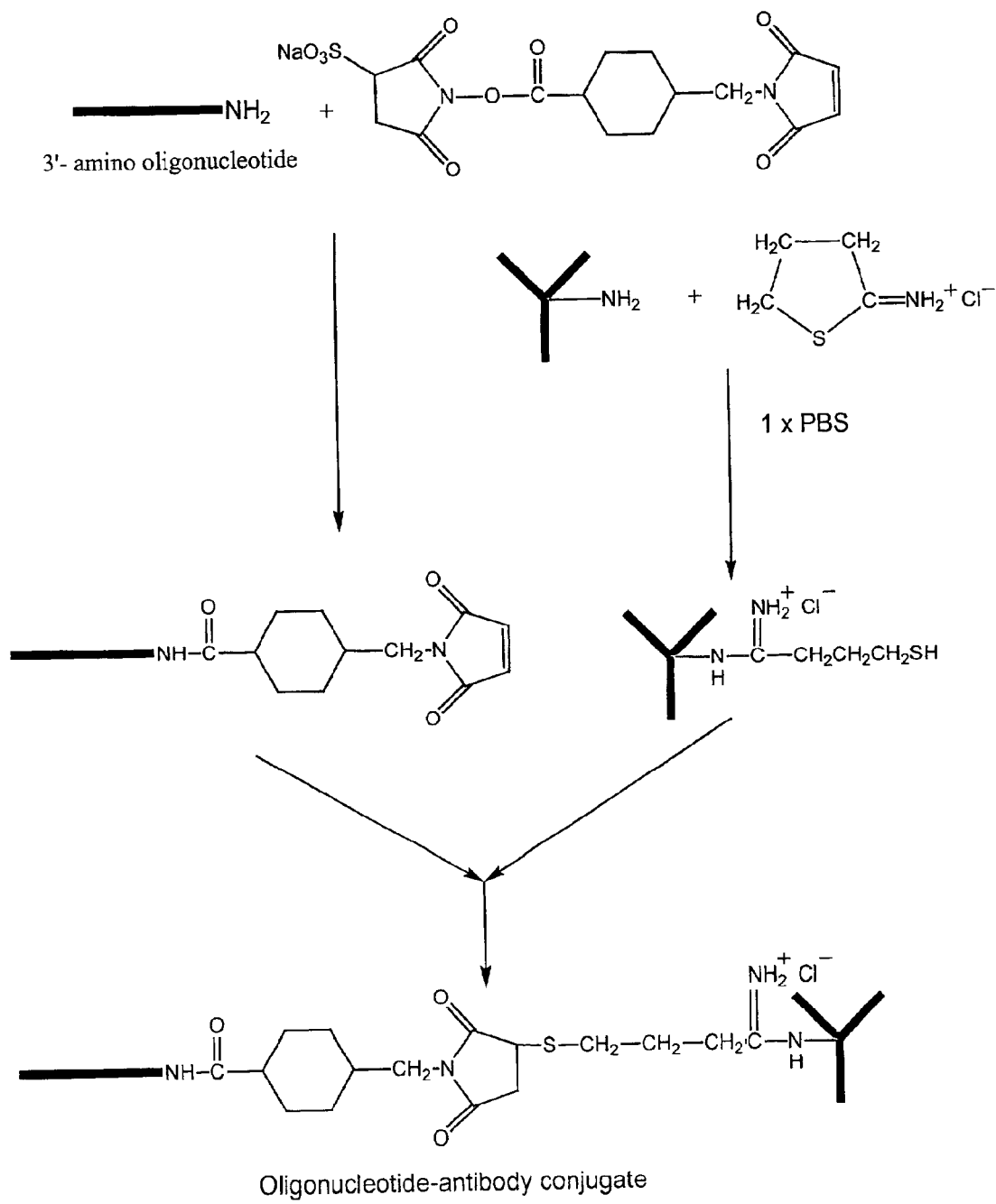
FIG. 1 illustrates the synthesis of an oligonucleotide-antibody conjugate. The preparation begins with the synthesis of the 3'-amino oligonucleotide that is activated with a hetero-bifunctional linker sulfo SMCC. Antibodies are then thiolated using Traut's reagent (iminothiolane). The activated oligonucleotide and thiolated antibodies are subsequently mixed to facilitate coupling of oligonucleotide to antibody.

The present invention relates to an improved method for forming a protein-oligonucleotide conjugate. The invention further concerns the conjugate molecules produced using such improved methods.

The reactions involve the covalent coupling of a thiolated amino group of a protein with an aminated group of an oligonucleotide. The oligonucleotides that can be employed in accordance with the present invention may vary from 2 nucleotides in length to over several thousand nucleotides in length, and can have any sequence. The oligonucleotides may be single-stranded or double-stranded, and may comprise naturally occurring nucleotide residues or may comprise modified In accordance with the most preferred embodiments of the present invention (see FIG. 1), the synthesis of the oligonucleotide-protein conjugate is accomplished in four steps:

1. Synthesis of an oligonucleotide having an amino group;
2. Activation of the 3' amino group by a heterofunctional linker;
3. Thiolation of an amino group of the protein to be coupled; and
4. Coupling of the activated oligonucleotide and the thiolated protein.

Such a procedure is simpler, and provides higher yields than the method of Yarmush et al. in which a thiol group is introduced at the 5' or 3' end of oligonucleotide and the thiolated oligonucleotide is then reacted with a protein via disulfide bond conjugation chemistry (Yarmush, M. L. et al., Bioconjugate Chemistry 8:935–940 (1997)). It is likewise superior to the method of Hendrickson et al. in which a 5' amino oligonucleotide (activated with N~succinimidyl thioacetate) is conjugated to an antibody that has been derivatized with sulfo-SMCC (Hendrickson, R. E. et al., Nucl., Acids Res. 23:522–529 (1994)), as well as to the method of Reddy et al. and Keller et al. in which a 5' or 3' amino oligonucleotide activated with 1,4 phenylene di-isothiocyanate is reacted with an antibody (Reddy, M. P. et al., U.S. Pat. No. 5,648,213 and Keller, G. H. et al., DNA Probes, MacMillan Publishers, Ltd. 1989) or an Fab' fragment of an antibody and coupled together using SMCC chemistry (Reddy, M. P. et al., U.S. Pat. No. 5,648,213).

The amino group of the oligonucleotide may be present at the 3' terminal residue of the oligonucleotide, at the 5' terminal residue of the oligonucleotide, or at a site between the termini of the molecule (i.e., an internal site).

The synthesis of an oligonucleotide having an amino group is preferably accomplished using an amino modifier reagent such as C7 CPG (Glen Research, Sterling Va.):

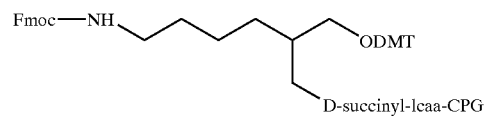

In order to link the modified oligonucleotide to the protein, a heterofunctional linker is employed. Preferably, such heterofunctional linker will have one moiety (such as an NHS-ester moiety) that is able to react with the primary amine of the 3' amino oligonucleotide and a second moiety (such as a maleimide group) that is capable of reacting with a thiol group. Examples of suitable heterofunctional linkers include:

| | |
|---|---|
| Sulfo-SMCC | sulfosuccinimidyl 4-(N-maleimidomethyl)cyclo-hexane-1-carboxylate |
| Sulfo-EMCS | N-(ε-Maleimidocaproyloxy) sulfosuccinimide ester |
| Sulfo-GMBS | (N-(γ-Maleimidobutyryloxy) sulfosuccinimide ester |
| Sulfo-KMUS | N-(K-Maleimidoundecanecanoyloxy) sulfosuccinimide ester |
| Sulfo-LC-SPDP | sulfosuccinimidyl 6-(3'-(2-pyridyldithio)-propionamido)hexanoate |
| Sulfo-MBS | m-Maleimidobenzoyl-N-hydroxysulfosuccinimide ester |
| Sulfo-SIAB | sulfosuccinimidyl(4-iodoacetyl)aminobenzoate |
| Sulfo-SMPB | sulfosuccinimidyl 4-(p-maleimidophenyl)butyrate |
| Sulfo-LC-SMPT | sulfosuccinimidyl-6-(α-methyl-α-(2-pyridyldithio)toluamido)hexanoate |
| SVSB | (N-succinimidyl-4-vinylsulfonyl)benzoate |
| SIA | N-succinimidyl iodoacetate or iodoacetic acid N-hydroxysuccinimide ester |
| SIACX | (succinimidyl 6-(4-iodoacetyl)amino methyl-cyclo-hexane-1-carbonyl)amino hexanoate |

| | |
|---|---|
| SIAXX | succinimidyl 6(6-(((iodoacetyl)amino hexanoyl)aminohexanoate)) |
| NPIA | p-nitrophenyl iodoacetate |

All of these reagents can be purchased from Pierce, Rockford, Ill.). Sulfo-SMCC (sulfosuccinimidyl 4-(N-maleimidomethyl)cyclohexane-1-carboxylate) is a preferred heterofunctional linker. The use of this compound is described by Samoszuk, M. K., et al. ("A peroxide-generating immunoconjugate directed to eosinophil peroxidase is cytotoxic to Hodgkin's disease cells in vitro," Antibody, Immunoconjugates Radiopharmaceuticals 2(1), 37–45 (1989));

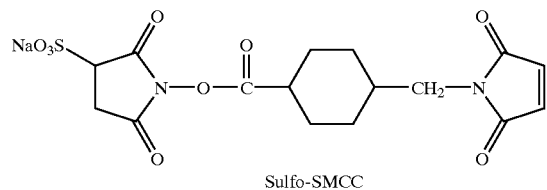

Sulfo-SMCC

Preferably, the linker is reacted with the amino oligonucleotide prior to its reaction with the protein. Reaction at a pH of approximately 8.0–8.5 at room temperature results in the formation of an amide bond between the amino group of the oligonucleotide and the ester carbon of the linker (FIG. 1).

The amino group of the protein that is to be conjugated is preferably reacted with iminothiolane (Traut's reagent). Reaction at room temperature results in the formation of a thiol modification to the involved amino group (FIG. 1). The amino group may be the amino terminal amino group, or it may be an internal amino group (e.g., the ε amino group of a lysine or arginine residue).

Coupling between the activated oligonucleotide and the thiolated protein is preferably accomplished by mixing the thiolated protein with the sulfo-SMCC-modified oligonucleotide. Such mixing may be conducted in phosphate buffered saline (PBS), 3 M NaCl, 2 mM EDTA.

Any protein bearing a free primary amino group can be conjugated in accordance with the methods of the present invention. Such proteins include enzymes, hormones, solubilized receptor proteins, peptides, immunoglobulins, etc.

In one embodiment, such proteins will be enzymes. By conjugating an enzyme to an oligonucleotide, the enzyme can be used to label (and hence identify the presence or concentration of) any nucleic acid molecule (DNA or RNA) in a sample that possesses a nucleotide sequence complementary in sequence to that of the conjugated oligonucleotide (see, for example, Kusunoki, S. et al., "Application of colorimetric microdilution plate hybridization for rapid genetic identification of 22 *Mycobacterium* species," J Clin Microbiol. 1991 August; 29(8):1596–603; Bhattacharya, S. et al., "Distinction of *Mycobacterium tuberculosis* from other mycobacteria through DNA hybridization," Indian J Med Res. 1988 Febuary; 87:144–50; Ezaki, T. "Rapid genetic identification system of mycobacteria," Kekkaku. 1992 December; 67(12):803–8; Ezaki, T. et al., "Quantitative microdilution plate hybridization to determine genetic relatedness among bacterial strains," Nippon Saikingaku Zasshi. 1990 September; 45(5):851–7; Ezaki, T. et al., "Simple genetic method to identify viridans group streptococci by colorimetric dot hybridization and fluorometric hybridization in microdilution wells," J Clin Microbiol. 1988 September; 26(9):1708–13; Cho, S. N. et al. "Colorimetric microwell plate hybridization assay for detection of amplified *Mycobacterium tuberculosis* DNA from sputum samples," J. Clin Microbiol. 1995 March; 33(3):752–4; Spargo, C. A. et al., "Chemiluminescent detection of strand displacement amplified DNA from species comprising the *Mycobacterium tuberculosis* complex," Mol Cell Probes. 1993 October; 7(5):395–404). Thus, the conjugates of the present invention may be used to detect the presence or absence of a nucleic acid sought to be detected in a biological medium, which may contain other nucleic acids that are not sought. Preferred methods for accomplishing such detection are described by Kourilsky et al. (U.S. Pat. Nos. 5,955,262; 5,876,928 and 5,605,800, all herein incorporate by reference) and by Avrameas et al. (U.S. Pat. No. 4,526,871)

Such samples may include biological samples derived from a human or other animal source (such as, for example, blood, stool, sputum, mucus, serum, urine, saliva, teardrop, a biopsy sample, a histology tissue sample, a PAP smear, a mole, a wart, an agricultural product, waste water, drinking water, milk, processed foodstuff, air, etc.) including samples derived from a bacterial or viral preparation, as well as other samples (such as, for example, agricultural products, waste or drinking water, milk or other processed foodstuff, air, etc.).

In one embodiment, the present invention provides a method for facilitating the detection of nucleic acid hybridization and amplification. Such assays may be used to identify alleles or polymorphisms (including single nucleotide polymorphisms), or may be used to reveal the presence of nucleic acid molecules that are characteristic of pathogens (e.g., viral DNA or RNA (such DNA or RNA of the hepatitis virus, immunodeficiency viruses (HIV, FIV), rubella, EBV, CMV, influenza, etc.), or bacterial/fungal DNA or RNA (e.g., DNA or RNA of *M. tuberculosi, Streptococcus pyogenes* Group A bacteria, *H. pylori, Chlamydia*, etc.).

For such purposes, enzymes such as alkaline phosphatase, β-galactosidase, horse radish peroxidase, urease, etc., for which chromogenic or fluorogenic substrates exist are particularly preferred. Suitable substrates for peroxidase include: TMB (3,3',5,5' tetramethyl-benzidine), DAB (3,3', 4,4' diaminobenzidine), and 4CN (4-chloro-1-naphthol), which produce insoluble products. Also suitable are TMB (dual function substrate), ABTS (2,2'-azino-di [3-ethylbenzthiazoline] sulfonate), and OPD (o-phenylenediamine), which produce soluble products. Suitable substrates for alkaline phosphatase include: BBT (2'-[2-benzthiazoyl]-6'-hydroxy-benzthiazole), 1,2-dioxetane chemiluminescent substrates, BCIP/NBT (5-bromo-4-chloro-3-indolyl phosphate/nitroblue tetrazolium), and p-NPP (p-nitrophenylphosphate). Suitable substrates for horse radish peroxidase include: Amplex™ Red reagent (10-acetyl-3,7-dihydroxyphenoxazine; Molecular Probes, Oregon), guaiac, 2-2'-azino-bis(3-ethyl-benthiazoline-6-sulfonic acid), tetramethylbenzidine, phenol, 4-aminoantipyrine, and 4,5-dihydroxynaphthalene-2,7-disulfonic acid (see also U.S. Pat. Nos. 6,251,621; 5,316,906; 5,443,986; and EP 0,641,351). In lieu of chromogenic substrates, enzymatic reactions may be followed by other means (changes in pH, production of product, etc.)

Although such enzymes are preferred, other enzymes can be similarly exploited, and a wide variety of chromogenic or fluorogenic substrates can be employed. For example, the carboxy terminus of single amino acids and short peptides can be conjugated to certain amine-containing fluorophores (e.g., rhodamine 110 (R110), etc.) to create fluorogenic peptidase substrates (Lucas, et al. (U.S. Pat. No. 5,698,411) and Landrum et al. (U.S. Pat. No. 5,976,822)). In addition 7-aminocoumarins (AMC) can be employed to form UV light-excitable substrates (e.g., CBZ-L-phenylalanyl-L-arginine amide of AMC) for serine proteases, including cathepsins, kallikrein and plasmin. The fluorogenic t-BOC-Leu-Met-CMAC substrate can be used to measure calpain activity. Many such substates are commercially available (Molecular Probes, Inc.).

The protein molecule of the conjugate can alternatively be a hapten (including an antigen) molecule or moiety, that can be recognized and bound by an immunoglobulin. Such molecules can be directly labeled, as with radioisotopes, fluors, chemiluminescent groups or enzymes. Alternatively, they may be reacted with a labeled molecule (for example a labeled binding ligand or second immunoglobulin capable of binding to the hapten or antigen). A wide variety of such haptens or antigens may be used (e.g., enzymatic co-factors, receptors, receptor ligands, hormones, cytokines, blood factors, viruses, steroids, drugs, etc.).

The protein molecule of the conjugate can alternatively be an immunoglobulin, which may be labeled directly (as with radioisotopes, fluors, chemiluminescent groups or enzymes), or indirectly (as by binding to a labeled molecule). As used herein, the term "immunoglobulin" includes natural or artificial mono- or polyvalent antibodies and polyclonal and monoclonal antibodies, and also molecules that are fragments and derivatives of such, including, for example, F(ab')$_2$, Fab' and Fab fragments, chimeric antibodies, hybrid antibodies having at least two antigen or epitope binding sites, single polypeptide chain antibodies, bispecific recombinant antibodies (e.g. quadromes, triomes), interspecies hybrid antibodies, and molecules that have been chemically modified and must be regarded as derivatives of such molecules and which may be prepared either by the known conventional methods of antibody production or by DNA recombination, using hybridoma techniques or antibody engineering or synthetically or semisynthetically in known manner. Methods for isolating or obtaining imnuunoglobulins are well-known in the art (Kohler, G. & Milstein, C., Nature 256:495–497 (1975); Taggart & Samloff, Science 219:1228–1230 (1983); Kozbor et al., Immunology Today 4:72–79 (1983); Morrison et al., Proc. Natl. Acad. Sci. USA 81:6851–6855 (1984); Takeda et al., Nature 314:452–454 (1985)); Biocca, S. et al., EMBO J. 9:101–108 (1990); Bird, R. E. et al., Science 242:423–426 (1988); Boss, M. A. et al., Nucl. Acids Res. 12:3791–3806 (1984); Boulianne, G. L. et al., Nature 312:643–446 (1984); Bukovsky, J. & Kennett, R. H., Hybridoma 6:219–228 (1987); Diano, M. et al., Anal. Biochem. 166:223–229 (1987); Huston J. S. et al., Proc. Natl. Acad. Sci. USA 85:5879–5883 (1988); Jones, P. T. et al., Nature 321:522–525 (1986); Langone, J. J. & Vunakis, H. V. (Editor), Methods Enzymol. 121, Academic Press, London (1987); Morrison, S. et al., Proc. Natl. Acad. Sci. USA 81:6851–6855 (1984); Oi, V. T. & Morrison, S. L., BioTechniques 4:214–221 (1986); Riechmann, L. et al., Nature 332:323–327 (1988); Tramontano, A. et al., Proc. Natl. Acad. Sci. USA 83:6736–6740 (1986); Wood, C. R. et al., Nature 314:446–449(1985); and Ladner, U.S. Pat. No. 4,946,778, issued Aug. 7, 1990.

Polyclonal antibodies may be produced through any of a variety of well known methods. For example, various animals may be immunized for this purpose in known manner by injecting them with an antigen (for example the target biological molecule, or another molecule sharing an epitope of the target biological molecule. Such antigen molecules may be of natural origin or obtained by DNA recombination or synthetic methods, or fragments thereof and the desired polyclonal antibodies are obtained from the resulting sera and purified by known methods. Alternatively, intact cells that array the target biological molecule may be used. Various adjuvants may also be used for increasing the immune response to the administration of antigen, depending on the animal selected for immunization. Examples of these adjuvants include Freund's adjuvant, mineral gels such as aluminum hydroxide, surfactant substances such as polyanions, peptides, oil emulsions, haemocyanins, dinitrophenol or lysolecithin.

If desired, the proteins used in the conjugates of the present invention may be purified to a desired degree of purity. Methods for accomplishing such purification are well known to those of ordinary skill (e.g. by immunoabsorption or immunoaffinity chromatography, by HPLC (High Performance Liquid Chromatography) or combinations thereof). Suitable antibody fragments may also be prepared by known methods. For example, F(ab')$_2$ fragments may be obtained by pepsin digestion of the complete polyclonal or monoclonal antibody. Fab' fragments may be obtained by reducing the disulfide bridges of the associated F(ab')$_2$ fragment, for example, and Fab fragments may be obtained, for example, by treating the antibody molecules with papain and a reducing agent.

Such immunoglobulins may be selected for their ability to bind to drugs, receptors, receptor ligands, tumor antigens, or antigens that are characteristic of pathogens (e.g., viruses such as hepatitis virus, immunodeficiency viruses (HIV, FIV), rubella, EBV, CMV, influenza, etc., or bacteria/fungi such as M. tuberculosi, Streptococcus pyogenes Group A bacteria, H. pylori, Chlamydia, etc.

In a second embodiment, the conjugates of the present invention may be used to assay for the presence of binding ligands to the conjugated protein, and the presence or concentration of such ligands detected using assays of nucleic acid amplification. Thus, for example, a conjugate can be prepared in which the protein is a receptor ligand. In the presence of the relevant receptor, the ligand portion of the conjugate will bind the receptor and thereby immobilize the conjugate. Such immobilization can be detected via nucleic acid amplification technologies, or nucleic acid molecular beacon technologies.

Any of a variety of nucleic acid amplification technologies may be employed, including polymerase chain reaction, ligase chain reaction, rolling circle amplification, strand displacement amplification, etc. (see, for example, EP-A-439 182; EP-A-320 308; 4,683,194; U.S. Pat. Nos.: 4,683, 202; 5,270,184; 5,427,930; 5,455,166; 5,733,733; 5,854, 033; 6,124,120; 6,143,495; 6,180,338; 6,207,368; 6,218, 152; 6,261,808). Additionally, signal amplification technologies such as branched chain nucleic acid amplification, and molecular beacon technology may be employed (see, for example, U.S. Pat. Nos. 5,854,033; 5,989,823; 6,090,552; 5,552,541 and Tyagi, et al., "Molecular beacons: probes that fluoresce upon hybridization," Nature Biotechnol 14(3):303–8 (1996).

Having now generally described the invention, the same will be more readily understood through reference to the following examples, which are provided by way of illustration, and are not intended to be limiting of the present invention, unless specified.

EXAMPLE 1

Synthesis of Oligonucleotide-Protein Conjugate

An oligonucleotide-protein conjugate was synthesized in order to illustrate the principles of the present invention. For such illustration, an antibody that binds interleukin-8 (IL-8) (anti-human IL-8/CXCL8; (MAB208, R&D Systems, Minneapolis, Minn.)) was employed as the conjugating protein.

Synthesis Of 3'-Amino Oligonucleotide: A 30 residue long oligonucleotide was synthesized using 3' aminomodifier C7 CPG obtained from Glen Research (Part # 20-2957-01) on a 1 μm scale. The oligonucleotide was cleaved and deprotected using Ammonia/Methylamine(1:9) for 2 hours at room temperature and then desalted using a G-25 sephadex (1.5 cm×50 cm) column using water as an eluent. The oligonucleotide was analyzed via capillary electrophoresis.

Activation Of 3'-Amino Oligonucleotide With Sulfo-SMCC: 40 $Abs_{260}$ units of the above-described 3' aminomodified oligonucleotide was activated with 4.6 mg of Sulfo-SMCC in 1 ml of 0.1 M bicarbonate buffer, pH 8.2, for 1 hour at room temperature and then purified using a sephadex G-25 column (1.5 cm×50 cm) using water as an eluent.

Activation Of Antibody With Iminothiolane (Traut's Reagent): 2.5 mg of antibody was activated with iminothiolane (20 μl of a 2 mg/ml solution in 1×PBS) in 1 ml of 1×PBS and reacted at room temperature for 2 hours. The activated antibody was purified using a G-25 column (1.5 cm×50 cm; Amersham-Pharmaceia, Piscataway, N.J.), using 1×PBS, 5 mM EDTA as an eluent.

DNA Oligonucleotide-Antibody Conjugation: Activated antibody was mixed with the sulfo-SMCC-modified oligonucleotide. The final concentration was 1×PBS, 3 M NaCl, 2 mM EDTA. The resulting mixture was concentrated using centricon-3 for 3 hours and left to react at 12° C. for 1 day.

Purification Of Oligonucleotide Antibody Conjugates: The above-described Antibody-Oligonucleotide conjugate was purified on a size exclusion P-100 column (1.5 cm×20 cm), using 0.1 M Tris buffer, pH 7.2, 5 mM EDTA as an eluent. Fractions that contained the first band (which had an $A_{260}/A_{280}$ ratio of 1.0–1.2) were collected, mixed and then purified on a DEAE column with a salt gradient of from 0.05 M NaCl to 1.0 M NaCl. The yield of the conjugate was 50%. The conjugate was characterized on 8% PAGE and stained with stains all (1-Ethyl-2-[3-(1-ethylnaphtho[1,2-d]-thiazolin-2-ylidene)-2-methylpropenyl]-naphthol[1,2-d] thiazolium bromide; Sigma Chemical, St. Louis, Mo.).

Figure 2:
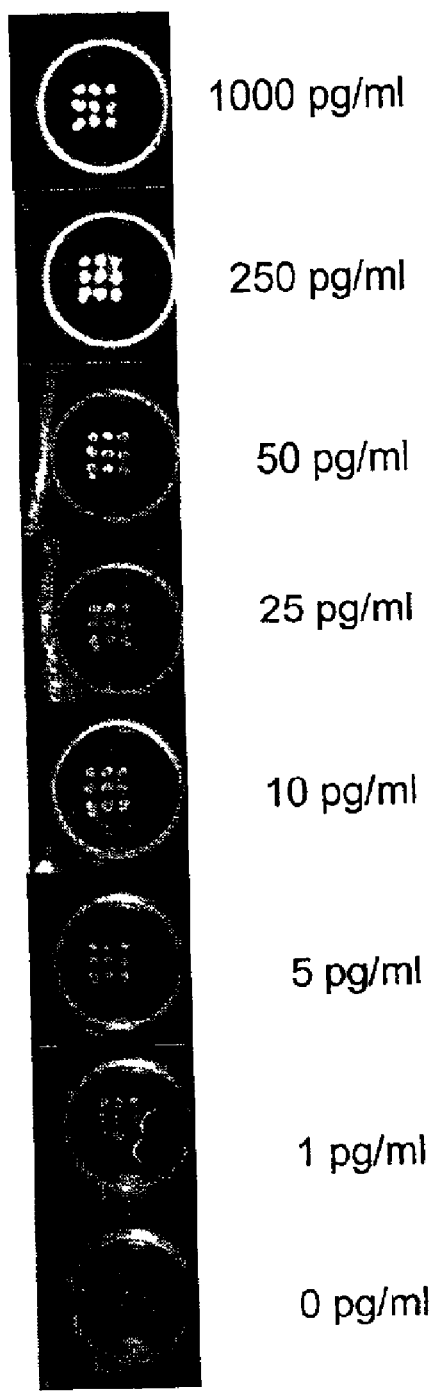
FIG. 2 illustrates the use of oligonucleotide-antibody conjugates in an IL 8 assay performed on an $A^2$ plate.

Immunoassay Protocol: The complementary oligonucleotide was printed on a 3×3 "Array of Array" ("$A^2$") plate. 140 ng of the Antibody-Oligonucleotide conjugate (in casein buffer with 0.5 M salt) was added to the well and incubated for 1 hr at 37° C. The plate is washed three times, and antigen is added in different concentrations ranging from 1,000 pg/ml to 1 pg/ml in 50 μl of volume. After three washings, a biotinylated second antibody conjugate is added and is allowed to react for 1 hour at 37° C. After three additional washings, porphyridium cruentun phycobilisome (SAv-PBXsl; Martek Biosciences, Columbia, Md.) is added and allowed to react for 1 hour. The plates are then washed three more times and imaged under a CCD camera. The sensitivity of the assay was found to be 1 pg/ml with IL-8 antigen (see FIG. 2).

EXAMPLE 2

Synthesis of Dye Labeled Oligonucleotide-Protein Conjugate

Procedure to Make Dye Labeled Oligo-Antibody Conjugate:
The synthesis of dye labeled oligonucleotide antibody conjugate involves the following steps:
Synthesis of 5' dye label 3'-amino oligonucleotide: A 30 mer oligonucleotide was synthesized on 3'-amino-modifier C7 CPG (Glen Research Part # 20-2957-01) on 1 μmole scale (coupling efficiency≅98%) on ABI 394 using $A^{pac}$, $G^{ipr-pac}$, $C^{ac}$ and T phosphoramdiites. At the 5' end Dye phosphoramidite (Cy3, or Cy3.5 or Cy5 or Cy5.5, purchased from Glen research, Sterling, Va.) was coupled using a standard protocol. The oligonucleotide was cleaved and deprotected using Ammonia for 24 hours at room temp. and purified on polypak cartridges (Glen research, Sterling, Va.). The dye labeled oligonucleotide was analyzed on CE (Beckman Pace 5000, with SSDNA gel kit).

Activation of 5'-dye label 3'-amino oligonucleotide with Sulfo SMCC: 40 ODs (Abs. 260 nm) of 5'-dye label 3'-amino oligonucleotide was activated with 4.6 mg of Sulfo SMCC in 1 ml of 0.1 M bicarbonate buffer, pH 8.2, for 1 hour at room temperature and purified on a Sephadex super fine DNA grade G-25 column (1.5 cm×50 cm) equilibrated with water. The desired fractions (total volume of about 6–8 ml) were mixed and the concentration was adjusted to 3 M salt (add solid NaCl), adjusted to 1×PBS (add 10×PBS); EDTA was added to a final concentration of 2 mM.

Activation of antibody with iminothiolane: 2.5 mg of antibody (IL8, IL4 or TNF) was dissolved in ~1ml of 1×PBS for at least 1 hour at room temperature and desalted on a Nap-25 column equilibrated with 1×PBS. Antibody was activated by adding iminothiolane (20 μl of 2 mg/ml solution in 1×PBS) to 1 ml of antibody in 1×PBS and reacted at room temperature for 2 hours. The activated antibody was purified on G-25 column (1.5 cm×50 cm) equilibrated with 1×PBS, 5 mM EDTA.

DNA oligonucleotide-Ab conjugation: Activated antibody was mixed with sulfo SMCC dye-labeled oligonucleotide, the final conc. was 1×PBS, 3 M NaCl, 2 mM EDTA. The mixture was transferred to 6–8 centricon-3, 2 ml in each centricon. The resulting mixture was concentrated for 2 hours at room temperature at 6000 rpm and then 3 hours at 12° C. at 6000 rpm and left to react for 1 day.

Purification of Oligonucleotide antibody conjugates: The Antibody-oligonucleotide conjugate was purified on size exclusion P-100 (Bio gel P-100 gel, 90–180 um, medium) column, 1.5 cm×20–22 cm equilibrated with 0.1 M tris buffer pH 7.4, 5 mM EDTA. Fractions containing the first peak were pooled ($A_{260}/A_{280}$ ratio=1.0–1.2), mixed, and purified on a DEAE (3 ml of gel) column. The sample was passed through the DEAE column 3–4 times and eluted with 0.1 M Tris pH 8.6 with salt gradient of 0.05 M NaCl, 0.1 M NaCl, 0.25 M NaCl, 0.5 M NaCl and 1 M NaCl. The fractions at 0.25 M and 0.5 M contain the conjugates. The yield of the conjugate was 50%. The conjugate was characterized by PAGE analysis.

All publications and patent applications mentioned in this specification are herein incorporated by reference to the same extent as if each individual publication or patent application had been specifically and individually indicated to be incorporated by reference. The discussion of the background to the invention herein is included to explain the context of the invention. Such explanation is not an admission that any of the material referred to was published, known, or part of the prior art or common general knowledge anywhere in the world as of the priority date of any of the aspects listed above.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method for producing an oligonucleotide-protein conjugate, wherein said method comprises the steps:
   (A) contacting an oligonucleotide having an amino group with a heterofunctional linker, wherein said linker has a first group reactive with said amino group and a second group reactive with a thiol group, said contacting being under conditions sufficient to permit said first group of said heterofunctional linker to become bonded to said amino group of said oligonucleotide, thereby forming an oligonucleotide-heterofunctional linker conjugate; and
   (B) contacting said oligonucleotide-heterofunctional linker conjugate (A) with a protein having a thiolated group reactive with said second group of said heterofunctional linker; wherein said thiolated group is formed by thiolation of an amino group of said protein; said contacting being under conditions sufficient to permit said thiolated group of said protein to become bonded to said second group of said heterofunctional linker of said oligonucleotide-heterofunctional linker conjugate, to thereby form said oligonucleotide-protein conjugate.

2. The method of claim 1, wherein said amino group of said oligonucleotide is at the 3' end of said oligonucleotide.

3. The method of claim 2, wherein step (A) additionally comprises forming said oligonucleotide having said 3' amino group.

4. The method of claim 2, wherein said oligonucleotide having said 3' amino group is formed by synthesizing said oligonucleotide on a 3'-amino CPG solid support.

5. The method of claim 1, wherein said amino group of said oligonucleotide is at the 5' end of said oligonucleotide.

6. The method of claim 1, wherein step (A) additionally comprises forming said oligonucleotide having said 5' amino group.

7. The method of claim 1, wherein said amino group of said oligonucleotide is at an internal site of said oligonucleotide.

8. The method of claim 7, wherein step (A) additionally comprises forming said oligonucleotide having said internal amino group.

9. The method of claim 1, wherein said modified amino group is C7 CPG.

10. The method of claim 1, wherein said first group of said heterofunctional linker is an NHS group.

11. The method of claim 1, wherein said second group of said heterofunctional linker is a maleimide group.

12. The method of claim 1, wherein said heterofunctional linker is selected from the group consisting of Sulfo-SMCC; Sulfo-EMCS; Sulfo-GMBS; Sulfo-KMUS; Sulfo-MBS; Sulfo-SIAB; Sulfo-SMPB; Sulfo-LC-SMPT; SVSB; SIACX; SIA, SIAXX; and NPIA.

13. The method of claim 12, wherein said heterofunctional linker is sulfo-SMCC.

14. The method of claim 1, wherein said thiolated group of said protein is derived from an iminothiolane moiety.

15. The method of claim 1, wherein step (B) additionally comprises forming said protein having said thiolated group.

16. The method of claim 15, wherein said thiolated group is formed by reacting the amino group of a protein with iminothiolane.

17. The method of claim 1, wherein said protein is an enzyme, hapten, immunoglobulin, streptavidin, avidin, or a phycobillin protein.

18. The method of claim 17, wherein said protein is an enzyme.

19. The method of claim 18, wherein said enzyme is selected from the group consisting of alkaline phosphatase, β-galactosidase, horse radish peroxidase, and urease.

20. The method of claim 17, wherein said protein is a hapten.

21. The method of claim 17, wherein said protein is an immunoglobulin.

22. The method of claim 21, wherein said immunoglobulin is an immunoglobulin that is able to bind to a drug, a receptor, a receptor ligand, or a tumor antigen.

23. The method of claim 21, wherein said immunoglobulin is able to bind an antigen that is characteristic of a pathogen.

24. The method of claim 23, wherein said pathogen is a virus.

25. The method of claim 24, wherein said pathogen is a bacteria or fungus.

26. The method of claim 17, wherein said protein is a streptavidin protein.

27. The method of claim 17, wherein said protein is an avidin protein.

28. The method of claim 17, wherein said protein is a phycobillin protein.

29. An oligonucleotide-protein conjugate produced through the process comprising:
   (A) contacting an oligonucleotide having an amino group with a heterofunctional linker, wherein said linker has a first group reactive with said amino group and a second group reactive with a thiol group, said contacting being under conditions sufficient to permit said first group of said heterofunctional linker to become bonded to said amino group of said oligonucleotide, thereby forming an oligonucleotide-heterofunctional linker conjugate; and
   (B) contacting said oligonucleotide-heterofunctional linker conjugate (A) with a protein having a thiolated group reactive with said second group of said heterofunctional linker; wherein said thiolated group is formed by thiolation of an amino group of said protein; said contacting being under conditions sufficient to permit said thiolated group of said protein to become bonded to said second group of said heterofunctional linker of said oligonucleotide-heterofunctional linker conjugate, to thereby form said oligonucleotide-protein conjugate.

30. The oligonucleotide-protein conjugate of claim 29, wherein said amino group of said oligonucleotide is at the 3' end of said oligonucleotide.

31. The oligonucleotide-protein conjugate of claim 29, wherein said amino group of said oligonucleotide is at the 5' end of said oligonucleotide.

32. The oligonucleotide-protein conjugate of claim 29, wherein said amino group of said oligonucleotide is at an internal site of said oligonucleotide.

33. The oligonucleotide-protein conjugate of claim 29, wherein said protein is an enzyme, hapten, immunoglobulin, streptavidin, avidin, or a phycobillin protein.

34. The oligonucleotide-protein conjugate of claim 33, wherein said protein is an enzyme.

35. The oligonucleotide-protein conjugate of claim 34, wherein said enzyme is selected from the group consisting of alkaline phosphatase, β-galactosidase, horse radish peroxidase, and urease.

36. The oligonucleotide-protein conjugate of claim 33, wherein said protein is a hapten.

37. The oligonucleotide-protein conjugate of claim 33, wherein said protein is an immunoglobulin.

38. The oligonucleotide-protein conjugate of claim 37, wherein said immunoglobulin is an immunoglobulin that is able to bind to a drug, a receptor, a receptor ligand, or a tumor antigen.

39. The oligonucleotide-protein conjugate of claim 37, wherein said immunoglobulin is able to bind an antigen that is characteristic of a pathogen.

40. The oligonucleotide-protein conjugate of claim 39, wherein said pathogen is a virus.

41. The oligonucleotide-protein conjugate of claim 39, wherein said pathogen is a bacteria or fungus.

42. The oligonucleotide-protein conjugate of claim 33, wherein said protein is a streptavidin protein.

43. The oligonucleotide-protein conjugate of claim 33, wherein said protein is an avidin protein.

44. The oligonucleotide-protein conjugate of claim 33, wherein said protein is a phycobillin protein.

45. A method for determining the presence or concentration of a target nucleic acid molecule in a sample which comprises:
   (I) contacting said sample with an oligonucleotide-protein conjugate, wherein a sequence of an oligonucleotide portion of said conjugate is selected to be able to hybridize with said target nucleic acid molecule, wherein said oligonucleotide-protein conjugate is produced through the process comprising:
      (A) contacting an oligonucleotide having an amino group with a heterofunctional linker, wherein said linker has a first group reactive with said amino group and a second group reactive with a thiol group, said contacting being under conditions sufficient to permit said first group of said heterofunctional linker to become bonded to said amino group of said oligonucleotide, thereby forming an oligonucleotide-heterofunctional linker conjugate; and
      (B) contacting said oligonucleotide-heterofunctional linker conjugate (A) with a protein having a thiolated group reactive with said second group of said heterofunctional linker; wherein said thiolated group is formed by thiolation of an amino group of said protein; said contacting being under conditions sufficient to permit said thiolated group of said protein to become bonded to said second group of said heterofunctional linker of said oligonucleotide-heterofunctional linker conjugate, to thereby form said oligonucleotide-protein conjugate;
   (II) detecting a protein portion of any of said oligonucleotide-protein conjugate having an oligonucleotide portion hybridized to said target nucleic acid molecule; wherein said detection determines the presence or concentration of said target nucleic acid molecule in said sample.

46. The method of claim 45, wherein said amino group of said oligonucleotide is at the 3' end of said oligonucleotide.

47. The method of claim 45, wherein said amino group of said oligonucleotide is at the 5' end of said oligonucleotide.

48. The method of claim 45, wherein said amino group of said oligonucleotide is at an internal site of said oligonucleotide.

49. The method of claim 45, wherein said protein of said oligonucleotide-protein is an enzyme, hapten, immunoglobulin, streptavidin, avidin, or a phycobillin protein.

50. The method of claim 49, wherein said protein is an enzyme.

51. The method of claim 50, wherein said enzyme is selected from the group consisting of alkaline phosphatase, β-galactosidase, horse radish peroxidase, and urease.

52. The method of claim 49, wherein said protein is a hapten.

53. The method of claim 49, wherein said protein is an immunoglobulin.

54. The method of claim 53, wherein said immunoglobulin is an immunoglobulin that is able to bind to a drug, a receptor, a receptor ligand, or a tumor antigen.

55. The method of claim 53, wherein said immunoglobulin is an immunoglobulin that is able to an antigen that is characteristic of a pathogen.

56. The method of claim 55, wherein said pathogen is a virus.

57. The method of claim 55, wherein said pathogen is a bacteria or fungus.

58. The method of claim 45, wherein said target nucleic acid molecule is a nucleic acid molecule of a pathogen.

59. The method of claim 45, wherein said target nucleic acid molecule is a nucleic acid molecule of a tumor cell.

60. The method of claim 49, wherein said protein is a streptavidin protein.

61. The method of claim 49, wherein said protein is an avidin protein.

62. The method of claim 49, wherein said protein is a phycobillin protein.

63. A method for determining the presence or concentration of a target analyte in a sample which comprises:
   (I) contacting said sample with an oligonucleotide-protein conjugate, wherein a protein portion of said conjugate is selected to be able to bind to said target analyte, wherein said oligonucleotide-protein conjugate is produced through the process comprising:
      (A) contacting an oligonucleotide having a 3' amino group with a heterofunctional linker, wherein said linker has a first group reactive with said 3' amino group and a second group reactive with a thiol group, said contacting being under conditions sufficient to permit said first group of said heterofunctional linker to become bonded to said 3' amino group of said oligonucleotide, thereby forming an oligonucleotide-heterofunctional linker conjugate; and
      (B) contacting said oligonucleotide-heterofunctional linker conjugate (A) with a protein having a thiolated group reactive with said second group of said heterofunctional tinker; wherein said thiolated group is formed by thiolation of an amino group of said protein; said contacting being under conditions sufficient to permit said thiolated group of said protein to become bonded to said second group of said heterofunctional linker of said oligonucleotide-heterofunctional linker conjugate, to thereby form said oligonucleotide-protein conjugate;
   (II) detecting an oligonucleotide portion of any of said oligonucleotide-protein conjugate having a protein portion bound to said target analyte; wherein said detection determines the presence or concentration of said target analyte in said sample.

64. The method of claim 63, wherein said amino group of said oligonucleotide is at the 3' end of said oligonucleotide.

65. The method of claim 63, wherein said amino group of said oligonucleotide is at the 5' end of said oligonucleotide.

66. The method of claim 63, wherein said amino group of said oligonucleotide is at an internal site of said oligonucleotide.

67. The method of claim 63, wherein said protein of said oligonucleotide-protein is an enzyme, receptor or receptor ligand.

68. The method of claim 67, wherein said protein is an enzyme.

69. The method of claim 67, wherein said protein is a receptor.

70. The method of claim 67, wherein said protein is a receptor ligand.

71. The method of claim 67, wherein said protein is a tumor antigen.

72. The method of claim 53, wherein said protein is characteristic of a pathogen.

73. The method of claim 72, wherein said pathogen is a virus.

74. The method of claim 72, wherein said pathogen is a bacteria or fungus.

* * * * *